United States Patent
Zhang et al.

(10) Patent No.: US 9,228,899 B2
(45) Date of Patent: Jan. 5, 2016

(54) TERAHERTZ TEMPORAL AND SPATIAL RESOLUTION IMAGING SYSTEM, IMAGING METHOD AND APPLICATION THEREOF

(71) Applicant: CAPITAL NORMAL UNIVERSITY, Beijing (CN)

(72) Inventors: Yan Zhang, Beijing (CN); Xinke Wang, Beijing (CN)

(73) Assignee: Capital Normal University, Beijing (CN)

(*) Notice: Subject to any disclaimer, the term of this patent is extended or adjusted under 35 U.S.C. 154(b) by 247 days.

(21) Appl. No.: 14/022,808

(22) Filed: Sep. 10, 2013

(65) Prior Publication Data

US 2014/0198973 A1   Jul. 17, 2014

(30) Foreign Application Priority Data

Jan. 15, 2013   (CN) .......................... 2013 1 0013686

(51) Int. Cl.
  *G01J 1/42*    (2006.01)
  *G01J 3/42*    (2006.01)
  *G01N 21/3586* (2014.01)

(52) U.S. Cl.
  CPC .............. *G01J 3/42* (2013.01); *G01N 21/3586* (2013.01)

(58) Field of Classification Search
  CPC ......... G01J 1/4257; G01J 1/0407; G01J 1/42; G01J 1/04; G06T 7/0004; G06T 7/00; G02F 2203/13; G01N 21/3586; G01N 21/3581
  See application file for complete search history.

(56) References Cited

U.S. PATENT DOCUMENTS

| | | | | |
|---|---|---|---|---|
| 4,734,576 A * | 3/1988 | Agoston et al. | ............... | 250/225 |
| 5,952,818 A * | 9/1999 | Zhang et al. | .................... | 324/96 |
| 6,111,416 A * | 8/2000 | Zhang et al. | ............... | 324/244.1 |
| 6,388,799 B1 * | 5/2002 | Arnone et al. | ................ | 359/326 |
| 6,414,473 B1 * | 7/2002 | Zhang et al. | .................... | 324/96 |
| 2001/0038074 A1 * | 11/2001 | Zhang et al. | ............... | 250/341.8 |

* cited by examiner

*Primary Examiner* — Marcus Taningco
(74) *Attorney, Agent, or Firm* — Buchanan Ingersoll & Rooney PC

(57) ABSTRACT

A terahertz temporal and spatial resolution imaging system is provided. The system includes: a sample placing rack; a detection crystal, located on the exit side of the sample placing rack; a pump light generating device, for generating a pump light to irradiate the test sample; a terahertz light generating device, for generating a terahertz light to irradiate the test sample, irradiate the detection crystal after obtaining information about the test sample, and modulate an index ellipsoid of the detection crystal; a detection light generating device, for generating a detection light to irradiate the detection crystal to detect the index ellipsoid of the detection crystal, thereby indirectly obtaining the information about the test sample; and an imaging apparatus, located in an optical path after the detection light passes through the detection crystal, for collecting terahertz images of the test sample.

40 Claims, 3 Drawing Sheets

TERAHERTZ TEMPORAL AND SPATIAL RESOLUTION IMAGING SYSTEM, IMAGING METHOD AND APPLICATION THEREOF

BACKGROUND OF THE INVENTION

1. Field of the Invention

The present invention relates to the field of optics, and in particular, to a terahertz temporal and spatial resolution imaging system, an imaging method and an application thereof.

2. Related Art

With development of semiconductor manufacturing processes and materials, electronic chips have a higher operation speed, a smaller area, and a lower cost. As phase transition of semiconductors with external excitation is determined by transport characteristics of carriers thereof, the study on the carrier transport phenomena is the foundation of semiconductor device research and development. The terahertz (referred to as THz) pulse technique, as a unique far-infrared measurement means, has demonstrated its significant application potential in the current scientific research and industrial detection. Especially in the study on the semiconductor carrier characteristics, as the terahertz pulse has a low photon energy, a narrow pulse width and other characteristics, which may not have a great impact on the carriers' concentration and transport and can achieve transient measurement, the terahertz time-resolved spectroscopy has become an indispensable research method in the semiconductor device research and development. FIG. 1 is a schematic optical view of the terahertz time-resolved spectroscopy used in the study on characteristics of carriers on semiconductors in the prior art. As shown in FIG. 1, a 800 nm near-infrared light I is used to pump semiconductor sample 101 and excite the light-induced characteristics thereof, then a terahertz pulse II interacts with the semiconductor sample 101, to carry sample transient information, and finally, a terahertz light II and a detection light III pass through a detection crystal 102; the terahertz pulse is measured via electro-optic sampling, to observe transient changes of the semiconductor. The terahertz measurement technique is coherent measurement, which can obtain amplitude and phase information of the spectrum simultaneously, so as to realize accurate analysis for semiconductor transient optical constants.

Owing to concentration gradient of the generated carriers on the semiconductor, horizontal and vertical diffusion may be formed. On one hand, during diffusion, the carriers may collide with each other for direct composite or interact with impurities contained in the semiconductor to form indirect composite. On the other hand, if there is an external electric field or a built-in electric field, the carriers may drift and may be scattered with the semiconductor ionized impurities and lattice vibrations. These processes will result in that the overall optical characteristics of semiconductors show unevenness. However, despite the traditional terahertz time-resolved spectroscopy has lots of advantages, due to its measurement constraints, it is necessary to focus the terahertz spot on one point on the sample for detection; thus, it only reflects the time-domain change characteristics of the carriers, but cannot exhibit the spatial distribution characteristics of the carriers caused by diffusion and drift phenomena.

SUMMARY OF THE INVENTION

An objective of the present invention is to overcome the limitation of using the traditional terahertz time-resolved spectroscopy to study evolution of semiconductor light-induced carriers, so as to realize the study on the spatial distribution characteristics thereof.

To achieve the objective, the present invention provides a terahertz temporal and spatial resolution imaging system, including:

a sample placing rack, for placing a test sample;

a detection crystal, located on the exit side of the sample placing rack;

a pump light generating device, for generating a pump light, where the pump light is used for irradiating the test sample to make the test sample generate light-induced results;

a terahertz light generating device, for generating a terahertz light, where the terahertz light is used for irradiating the test sample, irradiating the detection crystal after obtaining information about the test sample, and modulating an index ellipsoid of the detection crystal through an electro-optic effect;

a detection light generating device, for generating a detection light, where the detection light is used for irradiating the detection crystal to detect the index ellipsoid of the detection crystal, thereby indirectly obtaining the information about the test sample; and an imaging apparatus, located in an optical path after the detection light passes through the detection crystal, for receiving the detection light and collecting terahertz images of the test sample.

Preferably, the imaging apparatus is a charge-coupled device (CCD camera).

Preferably, the test sample is a Si semiconductor or a GaAs semiconductor.

Preferably, the detection crystal is adhered closely to the sample placing rack.

Preferably, the detection crystal is an electro-optic crystal having an electro-optic effect.

Preferably, the electro-optic crystal is a ZnTe crystal or a GaP crystal.

Preferably, the terahertz light generating device includes a terahertz-generation light generating device and a terahertz-generation crystal; the terahertz-generation light generating device being used for generating a terahertz-generation light; the terahertz-generation light being used for irradiating the terahertz-generation crystal to generate the terahertz light.

Preferably, the terahertz-generation crystal is a ZnTe crystal, a $LiNbO_3$ crystal or a GaAs crystal.

Preferably, the pump light generating device, the detection light generating device and the terahertz-generation light generating device are the same femtosecond pulse laser.

Preferably, a laser beam generated by the femtosecond pulse laser is a horizontally polarized light with a central wavelength of 800 nm, pulse duration of 50 fs, and a repetitive frequency of 1 kHz.

Preferably, the terahertz temporal and spatial resolution imaging system further includes:

a polarized beam splitter prism, located in an optical path of the horizontally polarized light, for splitting the horizontally polarized light into two beams of linearly polarized light whose polarization directions are perpendicular to each other, that is, a horizontally polarized light and a vertically polarized pump light;

a λ/2 wave plate, located on the incident side of the polarized beam splitter prism, for adjusting relative intensity of the horizontally polarized light and the pump light;

a polarized beam splitter prism, located in an optical path of the horizontally polarized light, for splitting the horizontally polarized light into two beams of linearly polarized light whose polarization directions are perpendicular to each other, that is, a horizontally polarized terahertz-generation light and a vertically polarized detection light; and a λ/2 wave plate, located on the incident side of the polarized beam splitter prism, for adjusting relative intensity of the terahertz-generation light and the detection light.

Preferably, the temporal and spatial resolution imaging system further includes a mechanical chopper in electrical connection with the imaging apparatus, for controlling the imaging apparatus to perform synchronous collection on terahertz images of the test sample. The mechanical chopper is located in the pump light path before the pump light irradiates the test sample, so as to modulate a repetitive frequency output by the pump light, or located in the terahertz-generation light path before the terahertz-generation light irradiates the terahertz-generation crystal, so as to modulate a repetitive frequency output by the terahertz-generation light.

Preferably, the temporal and spatial resolution imaging system further includes a first concave lens and a parabolic mirror, where the first concave lens and the parabolic mirror are used for performing beam expansion on the terahertz light; the first concave lens being located on the incident side of the terahertz-generation crystal; the parabolic mirror being located on the exit side of the terahertz-generation crystal.

Preferably, the temporal and spatial resolution imaging system further includes:

a λ/2 wave plate, located in the detection light path before the detection light irradiates the detection crystal, for controlling a polarization direction of the detection light; and a wave plate, located on the exit side of the λ/2 wave plate, for maintaining a polarization state of the detection light.

Preferably, the temporal and spatial resolution imaging system further includes a second concave lens and a third convex lens, where the second concave lens and the third convex lens are used for performing beam expansion on the detection light; the third convex lens being located in the detection light path before the detection light irradiates the detection crystal; the second concave lens being located in the focal plane on the incident side of the third convex lens.

Preferably, the temporal and spatial resolution imaging system further includes nano indium tin oxide (ITO) conductive glass, located on the incident side of the sample placing rack, for irradiating the pump light and the terahertz light onto the test sample after coincidence of the pump light and the terahertz light.

Preferably, the temporal and spatial resolution imaging system further includes a semi-reflective semi-transmissive mirror, located at an intersection of the detection light and optical axis of the detection crystal, for reflecting and transmitting the detection light with an equal proportion.

Preferably, the temporal and spatial resolution imaging system further includes:

a polarized beam splitter prism, located in the detection light path after the detection light transmits through the semi-reflective semi-transmissive mirror, for splitting the detection light transmitting through the semi-reflective semi-transmissive mirror into two beams of linearly polarized light whose polarization directions are perpendicular to each other;

a λ/4 wave plate, located on the incident side of the polarized beam splitter prism, for adjusting intensities of the two beams of linearly polarized light obtained through splitting;

a fourth convex lens, located on one side of the incident face of the polarized beam splitter prism, for converging the detection light transmitting through the semi-reflective semi-transmissive mirror; and a fifth convex lens, located on the exit side of the polarized beam splitter prism, for collimating the two beams of linearly polarized light obtained through splitting.

Preferably, the temporal and spatial resolution imaging system further includes a first motorized translation stage, located in the pump light path of the pump light, for successively changing an optical path difference between the pump light and the terahertz light.

Preferably, the temporal and spatial resolution imaging system further includes a second motorized translation stage, located in the terahertz light path or the detection light path, for successively changing an optical path difference between the terahertz light and the detection light.

The present invention further provides a terahertz temporal and spatial resolution imaging method, including:

placing a test sample on a sample placing rack;

irradiating the test sample with a pump light to make the test sample generate light-induced results;

irradiating the test sample with a terahertz light, the test sample modulating the terahertz electric field;

irradiating a detection crystal with the terahertz light, to modulate an index ellipsoid of the detection crystal;

irradiating the detection crystal with a detection light, to detect the index ellipsoid of the detection crystal and indirectly obtain information about the test sample;

adjusting a polarization state of the detection light to be a first polarization state, receiving the detection light by using an imaging apparatus, and measuring one polarization component $E_x$ of the terahertz electric field;

changing the polarization state of the detection light to be a second polarization state, and measuring the other polarization component $E_y$ of the terahertz electric field by using the imaging apparatus; and calculating relative intensity E according to the two measured polarization components $E_x$ and $E_y$ of the terahertz electric field, so as to obtain a terahertz image of the test sample.

Preferably, in the step of irradiating the test sample with the pump light to make the test sample generate light-induced results, the test sample is a Si semiconductor or a GaAs semiconductor; the pump light is a near-infrared femtosecond pulse with a central wavelength of 800 nm.

Preferably, the sample placing rack is adhered closely to an incident face of the detection crystal.

Preferably, after the step of irradiating the test sample with the pump light to make the test sample generate light-induced results, distribution of light-induced carriers is generated on the semiconductor sample.

Preferably, the step of irradiating the test sample with the terahertz light, the test sample modulating the terahertz electric field, specifically includes: increasing conductivity of the semiconductor sample by distribution of carriers generated on the semiconductor sample, resulting in increase of absorption of the semiconductor sample for the terahertz light, thereby causing decrease of transmissivity of the semiconductor sample for the terahertz light.

Preferably, after the step of irradiating the detection crystal with the terahertz light, to modulate the index ellipsoid of the detection crystal, modulation of the test sample on the terahertz light is reflected on the detection crystal.

Preferably, the step of irradiating the detection crystal with the detection light, to detect the index ellipsoid of the detection crystal and indirectly obtain the information about the test sample specifically includes: the detection light being incident on the detection crystal along a direction reverse collinear with the terahertz light; the polarization state of the detection light varying with changes of the index ellipsoid of the detection crystal; the detection light being vertically reflected by a surface of the detection crystal, and indirectly obtaining information about the terahertz light, that is, information about the test sample is obtained.

Preferably, the imaging apparatus is a CCD camera.

Preferably, the step of adjusting the polarization state of the detection light to be the first polarization state, receiving the detection light by using the imaging apparatus, and measuring one polarization component $E_x$ of the terahertz electric field specifically includes: adjusting the polarization state of the detection light by using a $\lambda/2$ wave plate, so that the detection light is in the first polarization state, and maintaining the polarization state by using a polarizer; splitting the detection light into two beams of linearly polarized detection light whose polarization directions are perpendicular to each other by using a polarized beam splitter prism; adjusting the polarization state of the detection light by using a $\lambda/4$ wave plate to make intensities of the two beams of linearly polarized detection light obtained through splitting equal; and receiving the two beams of linearly polarized detection light whose intensities are equal by using an imaging apparatus, and performing differential measurement with a terahertz differential imaging technique, to obtain the polarization component $E_x$ of the terahertz electric field.

Preferably, the step of performing the differential measurement with the terahertz differential imaging technique specifically includes: the imaging apparatus measuring components in a direction identical to that of electric fields of the two beams of linearly polarized detection light respectively, subtracting the two components collected, and indirectly obtaining one polarization component $E_x$ of the terahertz electric field.

Preferably, the step of adjusting the polarization state of the detection light to be the first polarization state, receiving the detection light by using the imaging apparatus, and measuring one polarization component $E_x$ of the terahertz electric field and the step of changing the polarization state of the detection light to be the second polarization state, and measuring the other polarization component $E_y$ of the terahertz electric field by using the imaging apparatus are reversible.

Preferably, in the step of adjusting the polarization state of the detection light to be the first polarization state, receiving the detection light by using the imaging apparatus, and measuring one polarization component $E_x$ of the terahertz electric field, polarization directions of the first polarization state and the terahertz light are parallel (that is, 0 degree of polarization) or perpendicular (that is, 90 degree of polarization) to each other.

Preferably, in the step of changing the polarization state of the detection light to be the second polarization state, and measuring the other polarization component $E_y$ of the terahertz electric field by using the imaging apparatus, polarization directions of the second polarization state and the first polarization state are at an angle of 45 degree or −45 degree.

Preferably, in the step of calculating the relative intensity E according to the two measured polarization components $E_x$ and $E_y$ of the terahertz electric field, so as to obtain the terahertz image of the test sample, the relative intensity E is calculated according to Formula $E=(|E_x|-|E_y|)/(|E_x|+|E_y|)$.

The present invention further provides an application of a terahertz temporal and spatial resolution imaging system, where the temporal and spatial resolution imaging system is used for studying a movement rule of semiconductor light-induced carriers, the studying including steps of:

selecting a test sample, using the temporal and spatial resolution imaging system for imaging measurement, and recording original experimental data;

using a digital holographic reconstruction algorithm for image reconstruction and optimization on the original experimental data, to obtain reconstructed image data; and extracting distribution of conductivity of the test sample from the optimized reconstructed image data, and analyzing the movement rule of light-induced carriers of the test sample.

Preferably, the test sample is a GaAs semiconductor.

Preferably, the step of using the temporal and spatial resolution imaging system for imaging measurement specifically includes: applying different-power pump light effects to semiconductors with one doping concentration, to perform imaging measurement respectively; or applying same-power pump light effects to semiconductors with different doping concentrations, to perform imaging measurement respectively; or applying different external bias electric fields to semiconductors with one doping concentration, to perform imaging measurement respectively; or applying the same external bias electric field to semiconductors with different doping concentrations, to perform imaging measurement respectively.

Preferably, the step of using the digital holographic reconstruction algorithm for image reconstruction and optimization on the original experimental data specifically includes: using an inverse diffraction digital image reconstruction algorithm for image reconstruction and optimization on the original image data.

Preferably, the inverse diffraction digital image reconstruction algorithm is an inverse Fresnel diffraction algorithm.

Preferably, the step of analyzing the movement rule of light-induced carriers of the test sample includes:

using a continuity equation to study a rule of diffusion movement of the semiconductor light-induced carriers, specifically, according to distribution of conductivity of semiconductors obtained from the step of applying different-power pump light effects to semiconductors with one doping concentration, to perform imaging measurement respectively or applying same-power pump light effects to semiconductors with different doping concentrations, to perform imaging measurement respectively, analyzing composite effect of light-induced carriers during diffusion, that is, influences of concentration gradient of the light-induced carriers and collision between the light-induced carriers on the diffusion movement of the light-induced carriers, estimating the service life of the semiconductor light-induced carriers, and analyzing proportions of the composite caused by direct collision between the light-induced carriers and the composite caused by lattice defects;

using a continuity equation to study a rule of drift movement of the semiconductor light-induced carriers, specifically, according to distribution of conductivity of semiconductors obtained from the step of applying different external bias electric fields to the semiconductors with one doping concentration, to perform imaging measurement respectively or applying the same external bias electric field to the semiconductors with different doping concentrations, to perform imaging measurement respectively, analyzing influences of intensity of external electric fields, the light-induced carriers, influences of scattering between impurities and phonons on drift movement of the light-induced carriers; and using a continuity equation to uniformly consider the diffusion movement and the drift movement of the semiconductor light-induced carriers, to analyze temporal and spatial distribution characteristics and semiconductor phase transition of the semiconductor light-induced carriers.

The terahertz temporal and spatial resolution imaging system and the terahertz temporal and spatial resolution imaging method in the embodiments of the present invention introduce a terahertz focal plane imaging technique into a terahertz time-resolved spectrum measurement system, that is, the terahertz time-resolved spectroscopy and the digital holography are organically combined to realize temporal and spatial resolution imaging measurement on light-induced characteristics of the test sample. By changing time delay between the terahertz light and the pump light and extracting terahertz spectrum constants, time-domain changes of the light-induced characteristics of the test sample are reflected; by using terahertz spots to irradiate different positions of the test sample, the spatial distribution rule of the light-induced characteristics of the test sample can be observed; terahertz two-dimensional information is loaded onto the polarization state of the detection light via electro-optic sampling, and is extracted by using an imaging apparatus in a differential detection approach. Such an imaging system can effectively shorten the test time and more truly reflect two-dimensional distribution of the terahertz electric field, thereby ultimately obtaining four-dimensional spectral information about the test sample, which achieves comprehensive and accurate observation for temporal and spatial evolution of the test sample and precisely renders a full view of phase transition of the test sample under ultrafast laser excitation.

DETAILED DESCRIPTION OF THE INVENTION

The technical solution of the present invention is further described below in detail with reference to the accompanying drawings and embodiments.

An imaging system according to the embodiments of the present invention, by introducing a terahertz focal plane imaging technique into a terahertz time-resolved spectrum measurement system, realizes temporal and spatial resolution imaging measurement on light-induced characteristics of the test sample (for example, distribution of semiconductor light-induced carriers); the system is applied to study on temporal and spatial characteristics of semiconductors under optical excitation, and optical digital holography is used for image reconstruction and optimization on original experimental data, thereby achieving comprehensive and accurate observation for temporal and spatial evolution of the semiconductor light-induced carriers.

Figure 1:
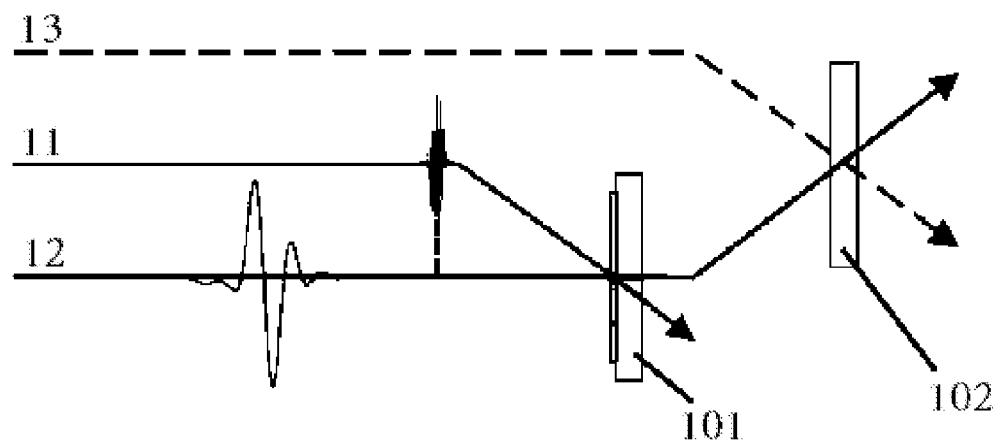
FIG. 1 is a schematic optical view of the terahertz time-resolved spectroscopy used in the study on characteristics of carriers on semiconductors in the prior art.
Figure 2:
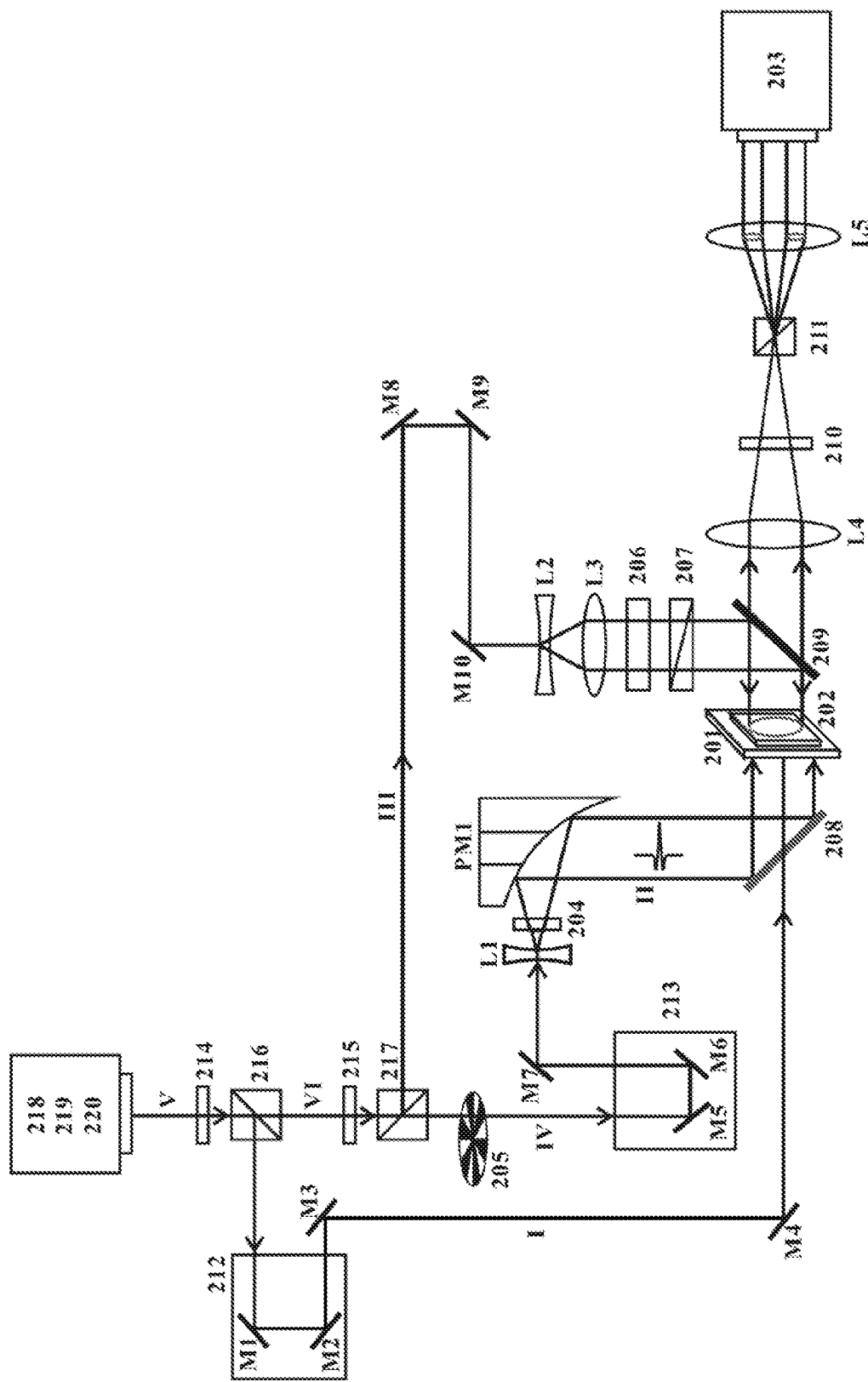
FIG. 2 is a schematic view of a terahertz temporal and spatial resolution imaging system according to an embodiment of the present invention.

FIG. 2 is a schematic view of a terahertz temporal and spatial resolution imaging system according to an embodiment of the present invention. As shown in FIG. 2, the imaging system includes: a sample placing rack 201, a detection crystal 202, an imaging apparatus 203, a pump light generating device 218, a terahertz light generating device, and a detection light generating device 219. The sample placing rack 201 is used for placing a test sample, where the test sample may be a Si semiconductor, a GaAs semiconductor or the like. The detection crystal 202 is an electro-optic crystal having an electro-optic effect, which may be a ZnTe crystal, a GaP crystal or the like. The detection crystal is located on the exit side of the sample placing rack; preferably, in the embodiment of the present invention, the detection crystal is adhered closely to the sample placing rack, so as to improve the imaging resolution. The pump light generating device 218 is used for generating a pump light I, where the pump light I is used for irradiating the test sample to excite the light-induced characteristics thereof. The pump light may be a near-infrared femtosecond pulse or a terahertz light pulse with a sub-picosecond pulse width. In the embodiment of the present invention, for example, when the test sample is a semiconductor, distribution of light-induced carriers may be generated if a near-infrared femtosecond pulse is used as the pump light to irradiate the test sample, where the single photon energy of the femtosecond pulse is greater than the band-gap energy of the test sample, so as to ensure excitation of the light-induced carriers. The terahertz light generating device is used for generating a terahertz light II, where the terahertz light II is used for first irradiating the test sample, irradiating the detection crystal after obtaining information about the test sample, and modulating an index ellipsoid of the detection crystal through an electro-optic effect. The information about the test sample therein indicates the distribution state of light-induced carriers or conductivity of a semiconductor sample. The terahertz light has a frequency in the range of 0.2-2.5 THz, and may be generated by a ZnTe crystal, a LiNbO$_3$ crystal or a GaAs crystal through a nonlinear optical rectification process, or may be generated by a photoconductive antenna. The spot size of the pump light I is less than that of the terahertz light, so as to ensure a sufficient field of view for observation of movement of the light-induced carriers. The detection light generating device 219 is used for generating a detection light III, where the detection light III is used for irradiating the detection crystal to detect the terahertz light, thereby indirectly obtaining the information about the test sample. The detection light III can adopt a near-infrared light pulse. The imaging apparatus 203 is located in an optical path after the detection light (III) passes through the detection crystal (202), which may use a CCD camera (charge-coupled device), for receiving the detection light and collecting terahertz images of the test sample, that is, electric field distribution images after the terahertz light transmits through the test sample. Subtraction is performed on the two images collected, and optical images are converted into a digital signal. The pump light spot is smaller than the terahertz light spot, so as to ensure a sufficient field of view for observation of the light-induced characteristics of the test sample.

The terahertz light generating device includes a terahertz-generation light generating device 220 and a terahertz-generation crystal 204, the terahertz-generation light generating device being used for generating a terahertz-generation light IV, the terahertz-generation light IV being used for irradiating the terahertz-generation crystal 204 to generate the terahertz light. The terahertz-generation light may be a near-infrared light pulse, and the terahertz-generation crystal may be a ZnTe crystal, a LiNbO$_3$ crystal or a GaAs crystal.

The imaging system further includes a mechanical chopper 205 in electrical connection with the imaging apparatus, for controlling the imaging apparatus 203 to perform synchronous collection. The mechanical chopper may be located in the terahertz light path before the terahertz-generation light irradiates the terahertz-generation crystal, so as to modulate a repetitive frequency output by the terahertz-generation light, or located in the pump light path before the pump light irradiates the test sample, so as to modulate a repetitive frequency output by the pump light.

The imaging system further includes a first concave lens L1 and a parabolic mirror PM1 for performing beam expansion on the terahertz light. The first concave lens L1 is located on the incident side of the terahertz-generation crystal; the parabolic mirror PM1 is located on the exit side of the terahertz-generation crystal.

The imaging system further includes a λ/2 wave plate 206 and a polarizer 207, where the λ/2 wave plate 206 is located in the detection light path before the detection light irradiates the detection crystal, for controlling a polarization direction of the detection light, and the polarizer 207 is located on the exit side of the λ/2 wave plate 206, for maintaining a polarization state of the detection light after passing through the λ/2 wave plate 206.

The imaging system further includes a second concave lens L2 and a third convex lens L3 for performing beam expansion on the detection light. The third convex lens L3 is located in the detection light path before the detection light (III) irradiates the detection crystal; the second concave lens L2 is located in the focal plane on the incident side of the third convex lens L3.

The imaging system further includes nano indium tin oxide (ITO) conductive glass 208, located on the incident side of the sample placing rack. The ITO conductive glass 208 can reflect the terahertz light and transmit the near-infrared light, so that the pump light and the terahertz light propagated along the direction shown in FIG. 2 are irradiated onto the test sample after coincidence.

The imaging system further includes a semi-reflective semi-transmissive mirror 209, located at an intersection of the detection light and optical axis of the detection crystal, for reflecting and transmitting the detection light with an equal proportion. For example, in the embodiment of the present invention, 50% of the detection light is reflected onto the detection crystal by the semi-reflective semi-transmissive mirror, so that, after obtaining terahertz light information and being reflected by a surface of the detection crystal, 50% of the reflected detection light reaches an imaging portion of the system through the semi-reflective semi-transmissive mirror.

The imaging system further includes a λ/4 wave plate 210, a polarized beam splitter prism 211, a fourth convex lens L4 and a fifth convex lens L5. The polarized beam splitter prism is located in the detection light path after the detection light transmits through the semi-reflective semi-transmissive mirror, for splitting the detection light transmitting through the semi-reflective semi-transmissive mirror into two beams of linearly polarized light whose polarization directions are perpendicular to each other, and achieving differential measurement on the imaging apparatus with a terahertz differential imaging technique, which can greatly optimize the signal to noise ratio of the system; the λ/4 wave plate is located on the incident side of the polarized beam splitter prism, for adjusting intensities of the two beams of linearly polarized light obtained through splitting to make the intensities of the two beams of light equal; the fourth convex lens L4 is located on the incident side of the polarized beam splitter prism, for converging the detection light to be incident on the polarized beam splitter prism; the fifth convex lens L5 is located on the exit side of the polarized beam splitter prism 211, for collimating the two beams of linearly polarized detection light respectively and then irradiating the collimated detection light onto the imaging apparatus for imaging measurement.

The imaging system further includes a first motorized translation stage 212, located in the pump light path, for successively changing an optical path difference between the pump light and the terahertz light. The first motorized translation stage includes plane reflecting mirrors M1 and M2, for changing the propagation direction of the pump light.

The imaging system further includes a second motorized translation stage 213, located in the terahertz light path or the detection light path, for successively changing an optical path difference between the terahertz light and the detection light. The second motorized translation stage includes plane reflecting mirrors M5 and M6, for changing the propagation direction of the terahertz light or the detection light.

Preferably, in the imaging system according to the embodiment of the present invention, the pump light generating device, the detection light generating device and the terahertz-generation light generating device are the same femtosecond pulse laser, that is, the pump light I, the detection light III and the terahertz-generation light IV are generated from a homologous femtosecond pulse laser. As shown in FIG. 2, the imaging system further includes λ/2 wave plates 214-215 and polarized beam splitter prisms 216-217. The polarized beam splitter prism 216 is used for splitting the horizontally polarized femtosecond pulse light V emitted from the laser into two beams of linearly polarized light whose polarization directions are perpendicular to each other, that is, a horizontally polarized light VI and a vertically polarized light I, where the vertically polarized light I is taken as a pump light. The λ/2 wave plate 214 is located on the incident side of the polarized beam splitter prism 216, for adjusting relative intensity of the horizontally polarized light VI and the vertically polarized light I. The polarized beam splitter prism 217 is located in an optical path of the horizontally polarized light VI, for re-splitting the horizontally polarized light VI into two beams of linearly polarized light whose polarization directions are perpendicular to each other, that is, a horizontally polarized light IV and a vertically polarized light III, where the horizontally polarized light is taken as a terahertz-generation light, and the vertically polarized light III is taken as a detection light. The λ/2 wave plate 215 is located on the incident side of the polarized beam splitter prism 217, for adjusting relative intensity of the horizontally polarized light IV and the vertically polarized light III.

The imaging system according to the embodiment of the present invention further includes reflecting mirrors M3-4 and M7-10 distributed at appropriate positions in the system, for changing the propagation direction of the beam.

The imaging system according to the embodiment of the present invention is provided with homologous pump light, detection light and terahertz-generation light by a Spectra-physics laser, and a femtosecond pulse laser emitted from the laser has a central wavelength of 800 nm, pulse duration of 50 fs, a repetitive frequency of 1 kHz, and single photon energy of 1.55 eV. Once the imaging system is modulated, the average power ranges of the pump light, the detection light and the terahertz-generation light are respectively 50-100 mW, 8-10 mW and 650-700 mW. The terahertz-generation crystal is a ZnTe crystal, and the terahertz light generated via optical rectification effect has an electric field intensity in the range of 5-10 kV/cm, and a frequency of 0.2-2.5 THz.

The imaging system according to the embodiment of the present invention mainly works as follows.

The femtosecond pulse laser passes through the λ/2 wave plate 214, the polarized beam splitter prism 216, the λ/2 wave plate 215 and the polarized beam splitter prism 217 sequentially after being emitted from the laser, and generates three beams after being split twice, which are a vertically polarized pump light, a vertically polarized detection light and a horizontally polarized terahertz-generation light. The pump light irradiates a test sample, for example, a semiconductor, to excite light-induced characteristics of the sample, generate particular distribution of light-induced carriers on the semiconductor sample. The horizontally polarized terahertz-generation light is incident on the terahertz-generation crystal, and a horizontally polarized terahertz light is generated through a nonlinear optical rectification process; the terahertz light, upon beam expansion, is incident on the semiconductor sample after coincidence with the propagation direction of the pump light through the ITO conductive glass, and the distribution of light-induced carriers on the semiconductor sample modulates wavefronts of the terahertz electric field. Therefore, the terahertz light passing through the semiconductor sample contains distribution characteristics of the light-induced carriers on the semiconductor sample. The terahertz light continues to irradiate the detection crystal, and modules an index ellipsoid of the detection crystal through an electro-optic effect. Meanwhile, the detection light, upon beam expansion, is reflected onto the detection crystal via the semi-reflective semi-transmissive mirror after the half-wave plate and the polarizer adjust its polarization state, and is propagated to an imaging portion of the system upon reflection by a surface of the detection crystal, and the polarization state of the emitted detection light varies with changes of the index ellipsoid of the detection crystal; thus, the detection light indirectly obtains information about the terahertz light, that is, distribution information about the light-induced carriers on the test sample is obtained. In the imaging portion, the detection light is incident on the polarized beam splitter prism upon convergence via the fourth convex lens and after the λ/4 wave plate adjusts its polarization state, is split into two linearly polarized beams whose polarization directions are perpendicular to each other and intensities are equal. The two linearly polarized beams are incident onto the imaging apparatus upon collimation via the fifth convex lens respectively, and the imaging apparatus uses a terahertz differential imaging technique for differential measurement and recording experimental data.

By using the terahertz temporal and spatial resolution imaging system according to the embodiment of the present invention, temporal and spatial resolution imaging can be performed on the test sample, so as to study the light-induced characteristics of the sample.

Figure 3:
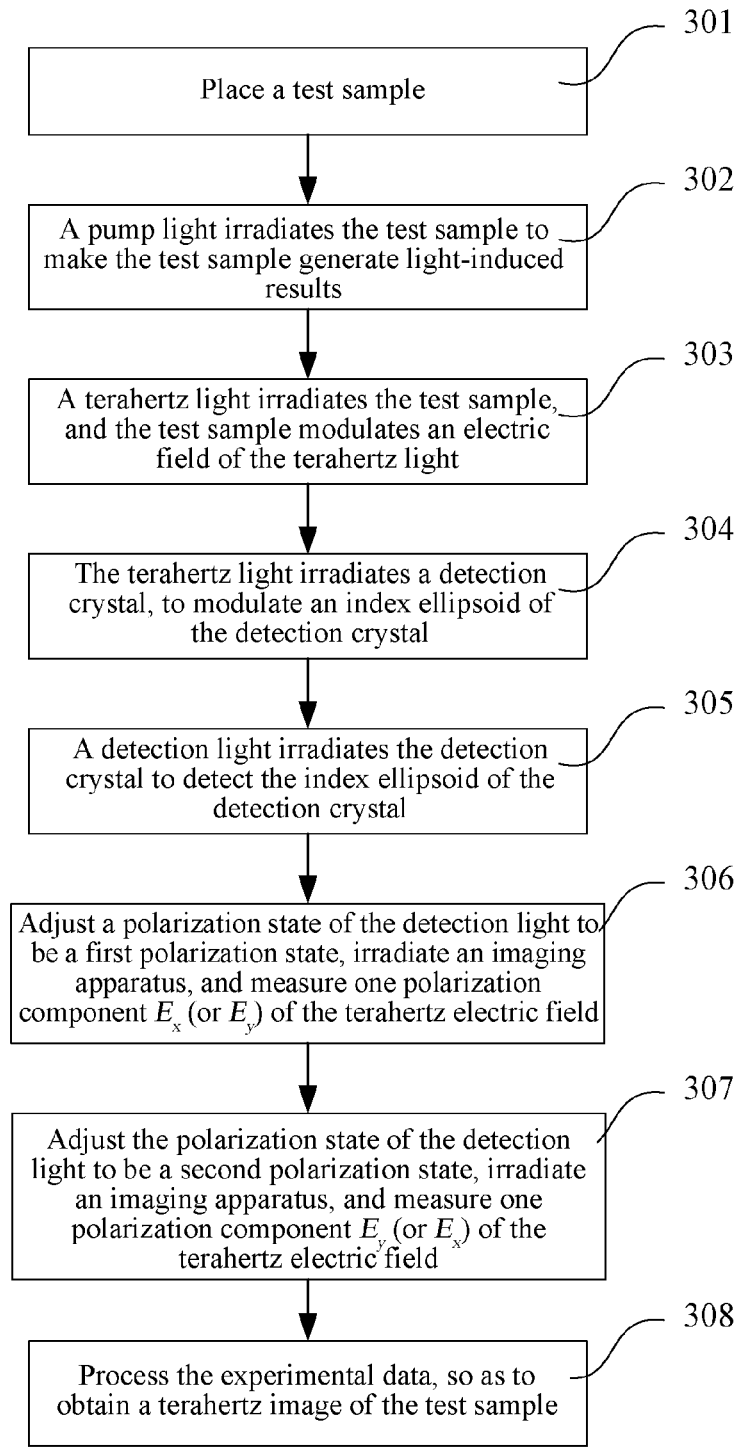
FIG. 3 is a flow chart of a terahertz temporal and spatial resolution imaging method according to an embodiment of the present invention.

FIG. 3 is a flow chart of a terahertz temporal and spatial resolution imaging method according to an embodiment of the present invention.

Step 301: Place a test sample, and put the test sample on a sample placing rack, where the test placing rack is located on the incident side of a detection crystal.

The test sample is a Si semiconductor or a GaAs semiconductor, and the sample placing rack according to the embodiment of the present invention is adhered closely to an incident face of the detection crystal, so as to ensure that near-field information of the terahertz light transmitting through the test sample can be obtained and to guarantee a higher image resolution.

Step 302: A pump light irradiates the test sample to make the test sample generate light-induced results.

The pump light may be a near-infrared femtosecond pulse or a terahertz light pulse with a sub-picosecond pulse width. Preferably, the pump light in the embodiment of the present invention is a near-infrared femtosecond pulse with a central wavelength of 800 nm. When the femtosecond pulse irradiates a semiconductor sample, valence band electrons of the semiconductor absorb photon energy, and transits to the conduction band, to form transient light-induced carriers, so the semiconductor sample generates particular distribution of the light-induced carriers. The distribution of the light-induced carriers results in that conductivity of the semiconductor sample increases and permittivity and permeability also change.

Step 303: A terahertz light irradiates the test sample in a collinear manner, thereby achieving modulation of the test sample on a terahertz electric field. Specifically, the terahertz light, upon beam expansion, is incident onto a test sample, for example, a semiconductor sample, after coincidence with the propagation direction of the pump light by using the ITO conductive glass; as the conductivity of the semiconductor sample increases, its absorption for terahertz pulses also increases, causing decrease of transmissivity of the semiconductor sample for the terahertz light, that is, distribution of light-induced carriers on the semiconductor sample modulates wavefronts of terahertz electric fields irradiating the semiconductor sample. Therefore, the terahertz light passing through the semiconductor sample contains distribution characteristics of the light-induced carriers on the semiconductor sample. The terahertz light may be generated by a near-infrared light pulse as a terahertz-generation light in a ZnTe crystal, a LiNbO$_3$ crystal or a GaAs crystal through a nonlinear optical rectification process, or may be generated by a photoconductive antenna.

The method according to the embodiment of the present invention uses a first concave lens L1 and a parabolic mirror PM1 to realize beam expansion on the terahertz light and make the pump light spot smaller than the terahertz light spot, so as to ensure a sufficient field of view for observation of movement of the light-induced carriers.

Step 304: The terahertz light irradiates a detection crystal, to modulate an index ellipsoid of the detection crystal. The terahertz light modulates the index ellipsoid of the detection crystal through an electro-optic effect, and modulation of the distribution of the light-induced carriers on the semiconductor sample on the terahertz light is reflected on the detection crystal.

Preferably, the detection crystal in the embodiment of the present invention is a ZnTe crystal.

Step 305: A detection light irradiates the detection crystal to detect the index ellipsoid of the detection crystal and indirectly obtain information about the test sample. Specifically, the detection light is incident onto the detection crystal along a direction a direction reverse to and collinear with the terahertz light, and is vertically reflected back through a surface of the detection crystal, and the polarization state of the reflected detection light varies with changes of the index ellipsoid of the detection crystal, so the detection light indirectly obtains information about the terahertz light, that is, information about the test sample, for example, information about distribution of light-induced carriers on the semiconductor sample, is obtained. The detection light may be a near-infrared light pulse.

In the method according to the embodiment of the present invention, before the detection light irradiates the detection crystal, a second concave lens L2 and a third convex lens L3 are used to perform beam expansion on the detection light, and half of the detection light is reflected to the detection crystal after the λ/2 wave plate 206 and the polarizer 207 modulate and maintain the polarization state thereof.

Step 306: Adjust a polarization state of the detection light to be a first polarization state, receive the detection light by using an imaging apparatus, and measure one polarization component $E_x$ (or $E_y$) of the terahertz electric field. Specifically, the λ/2 wave plate 206 is used to adjust the polarization state of the detection light to be in a first polarization state, and the polarization state thereof is maintained by the polarizer 207. After the detection light reflected back from the surface of the detection crystal passes through the semi-reflective semi-transmissive mirror once again, the transmitted detection light is propagated to the imaging portion of the system, is incident onto a polarized beam splitter prism 211 upon convergence via the fourth convex lens L4, and is split into two linearly polarized beams whose polarization directions are perpendicular to each other. Before the detection light reaches the polarized beam splitter prism, a λ/4 wave plate 210 is used to adjust the polarization state of the detection light to make intensities of the two beams of linearly polarized light equal. Two beams of linearly polarized detection light, upon collimation via the fifth convex lens L5 respectively, are incident onto an imaging apparatus (for example, a CCD camera). A first motorized translation stage 212 is used to successively change an optical path difference between the pump light and the terahertz light, a second motorized translation stage 213 is used to successively change an optical path difference between the terahertz light and the detection light, and an imaging apparatus uses a terahertz differential imaging technique for differential measurement on the detection light, that is, measure x (or y) component of electric fields both of the two beams of linearly polarized detection light modulated by the terahertz light, and subtract the two images collected, thereby indirectly obtaining the polarization component $E_x$ (or $E_y$) of the terahertz electric field modulated by distribution of light-induced carriers on the test sample.

Step 307: Change the polarization state of the detection light to be a second polarization state, and measure the other polarization component $E_y$ (or $E_x$) of the terahertz electric field.

Preferably, in the embodiment of the present invention, the first polarization state of the detection light is parallel (that is, 0 degree of polarization) or perpendicular (that is, 90 degree of polarization) to a polarization direction of the terahertz light, to measure the polarization component $E_x$ of the terahertz electric field. The second polarization state of the detection light is fixed in a polarization direction at an angle of 45 degree or −45 degree with the first polarization state, to measure the polarization component $E_y$ of the terahertz electric field.

The sequence of step 306 and step 307 can be reversed. There are two manners of using a second motorized translation stage for successively changing an optical path difference between the terahertz light and the detection light, one being to fix the detection light path, where the second motorized translation stage placed in the terahertz-generation light path successively changes the terahertz light path, and the other being to fix the terahertz light path, where the second motorized translation stage placed in the detection light path successively changes the detection light path. Preferably, the embodiment of the present invention adopts the manner of fixing the detection light path, where the second motorized translation stage placed in the terahertz-generation light path successively changes an optical path difference between two beams of light.

A mechanical chopper is placed on the incident side of the terahertz-generation crystal to modulate a repetitive frequency output by the terahertz-generation light, or the mechanical chopper is placed in a pump light path to modulate a repetitive frequency output by the pump light, and the mechanical chopper is electronically controlled, so as to control the imaging apparatus to perform synchronous collection on images.

Step 308: Process the experimental data, and calculate relative intensity E according to the two polarization components $E_x$ and $E_y$ of the terahertz electric field measured in step 306 and step 307, so as to obtain a terahertz image of the test sample. The relative intensity E is calculated according to Formula $E=(|E_x|-|E_y|)/(|E_x|+|E_y|)$.

Preferably, the imaging system according to the embodiment of the present invention is provided with homologous pump light, detection light and terahertz-generation light by a Spectra-physics laser, and a femtosecond pulse laser emitted from the laser has a central wavelength of 800 nm, pulse duration of 50 fs, a repetitive frequency of 1 kHz, and single photon energy of 1.55 eV. The femtosecond laser passes through the λ/2 wave plate 214, the polarized beam splitter prism 216, the λ/2 wave plate 215 and the polarized beam splitter prism 217 sequentially after being emitted from the laser, and generates three beams after being split twice, which are a vertically polarized pump light, a vertically polarized detection light and a horizontally polarized terahertz-generation light. By adjusting the λ/2 wave plates 214 and 215, the average power ranges of the pump light, the detection light and the terahertz-generation light are respectively 50-100 mW, 8-10 mW and 650-700 mW. The terahertz light is generated by the terahertz-generation light in a ZnTe crystal through an optical rectification process, and the terahertz light generated has an electric field intensity in the range of 5-10 kV/cm, and a frequency of 0.2-2.5 THz.

As stated above, the terahertz temporal and spatial resolution imaging system and the terahertz temporal and spatial resolution imaging method in the embodiments of the present invention introduce a terahertz focal plane imaging technique into a terahertz time-resolved spectrum measurement system, that is, the terahertz time-resolved spectroscopy and the digital holography are organically combined to realize temporal and spatial resolution imaging measurement on light-induced characteristics of the test sample. By changing time delay between the terahertz light and the pump light and extracting terahertz spectrum constants, time-domain changes of the light-induced characteristics of the test sample are reflected; by using terahertz spots to irradiate different positions of the test sample, the spatial distribution rule of the light-induced characteristics of the test sample can be observed; terahertz two-dimensional information is loaded onto the polarization state of the detection light via electro-optic sampling, and is extracted by using an imaging apparatus in a differential detection approach. Such an imaging system can effectively shorten the test time and more truly reflect two-dimensional distribution of the terahertz electric field, thereby ultimately obtaining four-dimensional spectral information about the test sample, which achieves comprehensive and accurate observation for temporal and spatial evolution of the test sample and precisely renders a full view of phase transition of the test sample under ultrafast laser excitation.

The temporal and spatial resolution imaging system in the embodiments of the present invention can be applied to study on temporal and spatial movement of semiconductor light-induced carriers, for example, diffusion movement and drift movement. The temporal and spatial resolution imaging system is used for imaging measurement by selecting an appropriate semiconductor sample, to obtain experimental data and perform image reconstruction and optimization, and extract the overall conductivity distribution of the semiconductor sample, which well studies the diffusion and drift movement rule of the semiconductor light-induced carriers. The study specifically includes the following steps.

Step 401: Select a test sample, use the temporal and spatial resolution imaging system for imaging measurement, and record original experimental data. The specific process is as follows.

At first, different-power pump lights are used to excite semiconductor samples with different doping concentrations, to perform imaging measurement respectively. For example, different-power pump light effects are applied to Si semiconductor samples with one doping concentration, and same-power pump light effects are applied to semiconductors with different doping concentrations, and by measuring diffusion of light-induced carriers in different situations, the overall conductivity distribution of the semiconductor sample is extracted from results of the measurement according to the method in the following step 402, the diffusion rule of the semiconductor light-induced carriers in different conditions is analyzed, and the composite effect of the light-induced carriers during diffusion is specifically analyzed, that is, influences of concentration gradient of the light-induced carriers and collision between the light-induced carriers on the diffusion movement of the light-induced carriers. In addition, the service life of the semiconductor light-induced carriers in different conditions and proportions of direct composite and indirect composite can be evaluated.

Next, different-intensity external terahertz electric fields are applied to semiconductor samples with different doping concentrations, to perform imaging measurement respectively. Specifically, two parallel electrodes are plated on a semiconductor, to apply a bias voltage; different external electric fields are applied to semiconductors with one doping concentration, and the same external electric field is applied to semiconductors with different doping concentrations. According to the method in the following step 402, the overall conductivity distribution of the semiconductor sample is extracted from results of the measurement, influences of impurities and phonons on scattering of the carriers are observed, and similarities and differences of spatial distribution situations of light-induced carriers indicated by nonlinear effects between the semiconductor conductivity and the external bias electric field in the process of improving intensity of the external electric field are analyzed, and attention is paid to influences of intervalley scattering on the overall distribution of the light-induced carriers after the field intensity is increased to a larger value.

Preferably, in the embodiment of the present invention, a compound with a low doping concentration, GaAs semiconductor, is selected, and it has a higher resistivity, has better transmission characteristics for terahertz pulses, and has higher light-induced carrier mobility and longer light-induced carrier service life, so as to facilitate observation of diffusion of the light-induced carriers, which can ensure observation of obvious drift movement of the light-induced carriers without causing short-circuit of the semiconductor.

Step 402: Use a digital holographic reconstruction algorithm for image reconstruction and optimization on the original experimental data, to obtain reconstructed image data.

As the wavelength of the terahertz light is longer, diffraction of electromagnetic waves always has influences on the image. To solve this problem, the embodiment of the present invention applies visible band digital holography to the field of terahertz, and optimizes the results of the measurement by selecting an appropriate inverse diffraction digital image reconstruction algorithm, to eliminate the influence of the diffraction on the image and improve the image definition, thereby providing high-quality experimental data for analysis of light-induced characteristics of the semiconductor.

Preferably, in the embodiment of the present invention, the terahertz electric field has a propagation distance of about several wavelengths in air and the detection crystal after passing through the semiconductor sample, and thus an inverse Fresnel diffraction algorithm is selected to reconstruct the collected image, according to the following inverse Fresnel diffraction integral formula, $$U(x_1, y_1) = -\frac{\exp(-jkd_{eff})}{j\lambda d_{eff}} \int\int_\infty U(x_0, y_0) \exp\left\{-j\frac{k}{2d_{eff}}[(x_0-x_1)^2 + (y_0-y_i)^2]\right\} dx_0 dy_0, \quad (1)$$

where $U(x_0, y_0)$ and $U(x_1, y_1)$ denote complex amplitudes of wave functions of the original image and the reconstructed image respectively, $(x_0, y_0)$ and $(x_1, y_1)$ denote observation plane coordinates of the original image and the reconstructed image respectively, k and $\lambda$ denote wave vector and wavelength of the terahertz electric field in vacuum respectively, and $d_{eff}$ denotes the diffraction distance, including the propagation distance of the terahertz light in the air and the detection crystal. The situation where each particular-wavelength image is processed for inversion of the terahertz electric field to the emergent face more clearly shows distribution of the light-induced carriers on the semiconductor. Through digital holographic reconstruction processing, the image quality has been significantly improved, which greatly improves the practicality of terahertz imaging.

Step 403: Extract transient optical constants of the sample from the image data according to the optimized reconstructed image data, and analyze the movement rule and temporal and spatial distribution characteristics of light-induced carriers on the semiconductor sample theoretically.

Preferably, the method in the embodiment of the present invention uses a continuity equation to perform theoretical simulation on diffusion movement and drift movement of the semiconductor sample, according to the following carrier continuity equation, $$\frac{\partial n}{\partial t} = D_n \frac{\partial^2 n}{\partial t^2} - \mu_n E_i \frac{\partial n}{\partial t} - \mu_n n \frac{\partial E_i}{\partial i} - \frac{\Delta n}{t} + g_n, \quad (2)$$

where n denotes the carrier concentration, t denotes the time, i=x, y, z denotes the spatial coordinate, $D_n$ denotes the carrier diffusion coefficient, $\mu_n$ denotes the carrier mobility, $E_i$ denotes components in various directions of the external bias electric field, $\tau$ denotes the carrier service life, and $g_n$ denotes the change of the carrier concentration caused by other factors. The continuity equation covers the basic characteristics of the carrier movement, the item on the left of the equation, that is, $$\frac{\partial n}{\partial t},$$

indicates the change of the local concentration of carriers with time; the first item on the right of the equation, that is, $$D_n \frac{\partial^2 n}{\partial t^2},$$

indicates the number of carriers accumulated in per unit time and per unit volume caused by diffusion, where the carrier diffusion coefficient $D_n$ reflects the size of the diffusion ability of nonequilibrium minority carriers; the second and third items on the right of the equation, that is, $$-\mu_n E_i \frac{\partial n}{\partial t} - \mu_n n \frac{\partial E_i}{\partial i},$$

indicate the number of carriers accumulated in per unit time and per unit volume caused by drift movement, where the carrier mobility $\mu_n$ is directly proportional to the carrier mean free time $\tau_n$, which reflects the probability of scattering of the carriers by impurities and phonons; the fourth item on the right, that is, $$\frac{\Delta n}{\tau},$$

indicates the number of carriers compositely disappearing in per unit time and per unit volume, where the carrier service life $\tau$ reflects the composite due to direct collision between the carriers or the probability of composite subject to lattice defects.

By using the continuity equation, the experimental data obtained above is analyzed theoretically, the composite effect of the semiconductor light-induced carriers during diffusion is analyzed, that is, influences of concentration gradient of the light-induced carriers and collision between the light-induced carriers on the diffusion movement of the light-induced carriers, the service life of the semiconductor light-induced carriers is evaluated, and proportions of the composite caused by direct collision between the light-induced carriers and the composite caused by lattice defects are analyzed; influences of intensity of external electric fields, the light-induced carriers, influences of scattering between impurities and phonons on drift movement of the light-induced carriers are analyzed, thereby disclosing the physical rule of diffusion movement and drift movement of the light-induced carriers; the diffusion movement and the drift movement of the semiconductor light-induced carriers are uniformly considered, and temporal and spatial distribution characteristics and overall semiconductor phase transition of the semiconductor light-induced carriers are analyzed, so as to probe the physical mechanism therein. In addition, experimental parameters are substituted in the continuity equation for numerical simulation, and the parameters are compared with the measured results, so as to verify accuracy of the experiment.

As stated above, the present invention applies a terahertz temporal and spatial resolution imaging system to study on temporal and spatial distribution characteristics of semiconductor light-induced carriers, obtains four-dimensional spectral information about the semiconductor light-induced carriers through imaging measurement, analyzes transport states of the light-induced carriers of the semiconductors with various doping concentrations under the effects of different-power pump lights and different-intensity external bias electric fields, and utilizes optical digital holography for image reconstruction and optimization on the original experimental data, so as to achieve comprehensive and accurate observation for temporal and spatial evolution of the light-induced carriers, and provide a complete experimental basis for people to recognize the semiconductor characteristics. In addition, the present invention uses a continuity equation for theoretical simulation, and analyzes the rule of diffusion movement and drift movement of the light-induced carriers in different external conditions, thereby analyzing the temporal and spatial evolution of semiconductor optical constants and disclosing the temporal and spatial characteristics of phase transition of the semiconductor under optical excitation, which lays a foundation for further studying various nonlinear processes of the semiconductor light-induced carriers appearing under the effects of electric fields and lattices. In the field of applications, the method in the embodiments of the present invention may show a new idea for development of the semiconductor device, such as avalanche photodiodes, solar cells, and semiconductor lasers.

The objectives, technical solutions, and beneficial effects of the present invention have been described in further detail through the above specific embodiments. It should be understood that the above descriptions are merely specific embodiments of the present invention, but not intended to limit the protection scope of the present invention. Any modification, equivalent replacement, or improvement made without departing from the spirit and principle of the present invention should fall within the protection scope of the present invention.

What is claimed is:

1. A terahertz temporal and spatial resolution imaging system, comprising:
   a sample placing rack, for placing a test sample;
   a detection crystal, located on the exit side of the sample placing rack;
   a pump light generating device, for generating a pump light, wherein the pump light is used for irradiating the test sample to make the test sample generate light-induced results;
   a terahertz light generating device, for generating a terahertz light, wherein the terahertz light is used for irradiating the test sample, irradiating the detection crystal after obtaining information about the test sample, and modulating an index ellipsoid of the detection crystal through an electro-optic effect;
   a detection light generating device, for generating a detection light, wherein the detection light is used for irradiating the detection crystal to detect the index ellipsoid of the detection crystal, thereby indirectly obtaining the information about the test sample; and
   an imaging apparatus, located in an optical path after the detection light passes through the detection crystal, for receiving the detection light and collecting terahertz images of the test sample.

2. The terahertz temporal and spatial resolution imaging system according to claim 1, wherein the imaging apparatus is a charge-coupled device camera.

3. The terahertz temporal and spatial resolution imaging system according to claim 1, wherein the test sample is a Si semiconductor or a GaAs semiconductor.

4. The terahertz temporal and spatial resolution imaging system according to claim 1, wherein the detection crystal is adhered closely to the sample placing rack.

5. The terahertz temporal and spatial resolution imaging system according to claim 1, wherein the detection crystal is an electro-optic crystal having an electro-optic effect.

6. The terahertz temporal and spatial resolution imaging system according to claim 5, wherein the electro-optic crystal is a ZnTe crystal or a GaP crystal.

7. The terahertz temporal and spatial resolution imaging system according to claim 1, wherein the terahertz light generating device comprises a terahertz-generation light generating device and a terahertz-generation crystal;
   the terahertz-generation light generating device being used for generating a terahertz-generation light;
   the terahertz-generation light (IV) being used for irradiating the terahertz-generation crystal to generate the terahertz light.

8. The terahertz temporal and spatial resolution imaging system according to claim 7, wherein the terahertz-generation crystal is a ZnTe crystal, a LiNbO$_3$ crystal or a GaAs crystal.

9. The terahertz temporal and spatial resolution imaging system according to claim 7, wherein the pump light generating device, the detection light generating device and the terahertz-generation light generating device are the same femtosecond pulse laser.

10. The terahertz temporal and spatial resolution imaging system according to claim 9, wherein a laser beam generated by the femtosecond pulse laser is a horizontally polarized light with a central wavelength of 800 nm, pulse duration of 50 fs, and a repetitive frequency of 1 kHz.

11. The terahertz temporal and spatial resolution imaging system according to claim 10, wherein the terahertz temporal and spatial resolution imaging system comprises:
    a first polarized beam splitter prism, located in an optical path of the horizontally polarized light, for splitting the horizontally polarized light into two beams of linearly polarized light whose polarization directions are perpendicular to each other, that is, a horizontally polarized light and a vertically polarized pump light;
    a first λ/2 wave plate, located on the incident side of the polarized beam splitter prism, for adjusting relative intensity of the horizontally polarized light and the pump light;
    a second polarized beam splitter prism, located in an optical path of the horizontally polarized light, for splitting the horizontally polarized light into two beams of linearly polarized light whose polarization directions are perpendicular to each other, that is, a horizontally polarized terahertz-generation light and a vertically polarized detection light; and
    a second λ/2 wave plate, located on the incident side of the polarized beam splitter prism, for adjusting relative intensity of the terahertz-generation light and the detection light.

12. The terahertz temporal and spatial resolution imaging system according to claim 1, wherein the temporal and spatial resolution imaging system further comprises a mechanical chopper, in electrical connection with the imaging apparatus, for controlling the imaging apparatus to perform synchronous collection on the terahertz images of the test sample.

13. The terahertz temporal and spatial resolution imaging system according to claim 12, wherein the mechanical chopper is located in the pump light path before the pump light irradiates the test sample, so as to modulate a repetitive frequency output by the pump light, or located in the terahertz-generation light path before the terahertz-generation light irradiates the terahertz-generation crystal, so as to modulate a repetitive frequency output by the terahertz-generation light.

14. The terahertz temporal and spatial resolution imaging system according to claim 1, wherein the temporal and spatial resolution imaging system further comprises a first concave lens and a parabolic mirror, wherein the first concave lens and the parabolic mirror are used for performing beam expansion on the terahertz light;
    the first concave lens being located on the incident side of the terahertz-generation crystal;
    the parabolic mirror being located on one the exit side of the terahertz-generation crystal.

15. The terahertz temporal and spatial resolution imaging system according to claim 1, wherein the temporal and spatial resolution imaging system further comprises:
    a third λ/2 wave plate, located in the detection light path before the detection light irradiates the detection crystal, for controlling a polarization direction of the detection light; and
    a polarizer located on the exit side of the third λ/2 wave plate, for maintaining a polarization state of the detection light.

16. The terahertz temporal and spatial resolution imaging system according to claim 1, wherein the temporal and spatial resolution imaging system further comprises: a second concave lens (L2) and a third convex lens (L3), wherein the second concave lens (L2) and the third convex lens (L3) are used for performing beam expansion on the detection light;
    the third convex lens (L3) being located in the detection light path before the detection light irradiates the detection crystal;
    the second concave lens (L2) being located in the focal plane on the incident side of the third convex lens (L3).

17. The terahertz temporal and spatial resolution imaging system according to claim 1, wherein the temporal and spatial resolution imaging system further comprises nano indium tin oxide (ITO) conductive glass, located on the incident side of the sample placing rack, for irradiating the pump light and the terahertz light onto the test sample after coincidence of the pump light and the terahertz light.

18. The terahertz temporal and spatial resolution imaging system according to claim 1, wherein the temporal and spatial resolution imaging system further comprises a semi-reflective semi-transmissive mirror, located at an intersection of the detection light and optical axis of the detection crystal, for reflecting and transmitting the detection light with an equal proportion.

19. The terahertz temporal and spatial resolution imaging system according to claim 1, wherein the temporal and spatial resolution imaging system further comprises:
    a third polarized beam splitter prism, located in the detection light path after the detection light transmits through the semi-reflective semi-transmissive mirror, for splitting the detection light transmitting through the semi-reflective semi-transmissive mirror into two beams of linearly polarized light whose polarization directions are perpendicular to each other;
    a λ/4 wave plate, located on the incident side of the polarized beam splitter prism, for adjusting intensities of the two beams of linearly polarized light obtained through splitting;
    a fourth convex lens, located on the incident side of the polarized beam splitter prism, for converging the detection light transmitting through the semi-reflective semi-transmissive mirror; and
    a fifth convex lens, located on the exit side the polarized beam splitter prism, for collimating the two beams of linearly polarized light obtained through splitting.

20. The terahertz temporal and spatial resolution imaging system according to claim 1, wherein the temporal and spatial resolution imaging system further comprises a first motorized translation stage, located in the pump light path, for successively changing an optical path difference between the pump light and the terahertz light.

21. The terahertz temporal and spatial resolution imaging system according to claim 1, wherein the temporal and spatial resolution imaging system further comprises a second motorized translation stage, located in the terahertz light path or the detection light path, for successively changing an optical path difference between the terahertz light and the detection light.

22. A terahertz temporal and spatial resolution imaging method, comprising:

placing a test sample on a sample placing rack;
irradiating the test sample with a pump light to make the test sample generate light-induced results;
irradiating the test sample with a terahertz light, the test sample modulating the terahertz electric field;
irradiating a detection crystal with the terahertz light, to modulate an index ellipsoid of the detection crystal;
irradiating the detection crystal with a detection light, to detect the index ellipsoid of the detection crystal and indirectly obtain information about the test sample;
adjusting a polarization state of the detection light to be a first polarization state, receiving the detection light by using an imaging apparatus, and measuring one polarization component $E_x$ of the terahertz electric field;
changing the polarization state of the detection light to be a second polarization state, and measuring the other polarization component $E_y$ of the terahertz electric field by using the imaging apparatus; and
calculating relative intensity E according to the two measured polarization components $E_x$ and $E_y$ of the terahertz electric field, so as to obtain a terahertz image of the test sample.

23. The terahertz temporal and spatial resolution imaging method according to claim 22, wherein, in the step of irradiating the test sample with the pump light to make the test sample generate the light-induced results, the test sample is a Si semiconductor or a GaAs semiconductor; the pump light is a near-infrared femtosecond pulse with a central wavelength of 800 nm.

24. The terahertz temporal and spatial resolution imaging method according to claim 22, wherein the sample placing rack is adhered closely to an incident face of the detection crystal.

25. The terahertz temporal and spatial resolution imaging method according to claim 23, wherein after the step of irradiating the test sample with the pump light to make the test sample generate the light-induced results, distribution of light-induced carriers is generated on the semiconductor sample.

26. The terahertz temporal and spatial resolution imaging method according to claim 23, wherein the step of irradiating the test sample with the terahertz light, the test sample modulating the terahertz electric field, specifically comprises: increasing conductivity of the semiconductor sample by distribution of carriers generated on the semiconductor sample, resulting in increase of absorption of the test sample for the terahertz light, thereby causing decrease of transmissivity of the test sample for the terahertz light.

27. The terahertz temporal and spatial resolution imaging method according to claim 22, wherein after the step of irradiating the detection crystal with the terahertz light, to modulate the index ellipsoid of the detection crystal, the modulation of the test sample on the terahertz light is reflected on the detection crystal.

28. The terahertz temporal and spatial resolution imaging method according to claim 22, wherein the step of irradiating the detection crystal with the detection light, to detect the index ellipsoid of the detection crystal and indirectly obtain the information about the test sample specifically comprises:
the detection light being incident on the detection crystal along a direction reverse to and collinear with the terahertz light;
the polarization state of the detection light varying with changes of the index ellipsoid of the detection crystal; and
the detection light being vertically reflected by a surface of the detection crystal, and indirectly obtaining information about the terahertz light, that is, the information about the test sample is obtained.

29. The terahertz temporal and spatial resolution imaging method according to claim 22, wherein the imaging apparatus is a charge-coupled device camera.

30. The terahertz temporal and spatial resolution imaging method according to claim 22, wherein the step of adjusting the polarization state of the detection light to be the first polarization state, receiving the detection light by using the imaging apparatus, and measuring one polarization component $E_x$ of the terahertz electric field specifically comprises:
adjusting the polarization state of the detection light by using a λ/2 wave plate, so that the detection light is in the first polarization state, and maintaining the polarization state by using a polarizer;
splitting the detection light into two beams of linearly polarized detection light whose polarization directions are perpendicular to each other by using a polarized beam splitter prism;
adjusting the polarization state of the detection light by using a λ/4 wave plate to make intensities of the two beams of linearly polarized detection light obtained through splitting equal; and
receiving the two beams of linearly polarized detection light whose intensities are equal by using an imaging apparatus, and performing differential measurement with a terahertz differential imaging technique, to obtain the polarization component $E_x$ of the terahertz electric field.

31. The terahertz temporal and spatial resolution imaging method according to claim 30, wherein the step of performing the differential measurement with the terahertz differential imaging technique specifically comprises: the imaging apparatus measuring components in a direction identical to that of electric fields of the two beams of linearly polarized detection light respectively, subtracting the two components collected, and indirectly obtaining one polarization component $E_x$ of the terahertz electric field.

32. The terahertz temporal and spatial resolution imaging method according to claim 22, wherein the step of adjusting the polarization state of the detection light to be the first polarization state, receiving the detection light by using the imaging apparatus, and measuring one polarization component $E_x$ of the terahertz electric field and the step of changing the polarization state of the detection light to be the second polarization state, and measuring the other polarization component $E_y$ of the terahertz electric field by using the imaging apparatus are reversible.

33. The terahertz temporal and spatial resolution imaging method according to claim 22, wherein, in the step of adjusting the polarization state of the detection light to be the first polarization state, receiving the detection light by using the imaging apparatus, and measuring one polarization component $E_x$ of the terahertz electric field, polarization directions of the first polarization state and the terahertz light are parallel (that is, 0 degree of polarization) or perpendicular (that is, 90 degree of polarization) to each other; and
in the step of changing the polarization state of the detection light to be the second polarization state, and measuring the other polarization component $E_y$ of the terahertz electric field by using the imaging apparatus, polarization directions of the second polarization state and the first polarization state are at an angle of 45 degree or −45 degree.

34. The terahertz temporal and spatial resolution imaging method according to claim 22, wherein, in the step of calculating the relative intensity E according to the two measured polarization components $E_x$ and $E_y$ of the terahertz electric field, so as to obtain the terahertz image of the test sample, the relative intensity E is calculated according to Formula $E=(|E_x|-|E_y|)/(|E_x|+|E_y|)$.

35. An application of the terahertz temporal and spatial resolution imaging system according to claim 1, wherein the temporal and spatial resolution imaging system is used for studying a movement rule of semiconductor light-induced carriers, the study comprising steps of:
- selecting a test sample, using the temporal and spatial resolution imaging system for imaging measurement, and recording original experimental data;
- using a digital holographic reconstruction algorithm for image reconstruction and optimization on the original experimental data, to obtain reconstructed image data; and
- extracting distribution of conductivity of the test sample from the optimized reconstructed image data, and analyzing the movement rule of light-induced carriers of the test sample.

36. The application of a terahertz temporal and spatial resolution imaging system according to claim 35, wherein the test sample is a GaAs semiconductor.

37. The application of a terahertz temporal and spatial resolution imaging system according to claim 35, wherein the step of using the temporal and spatial resolution imaging system for the imaging measurement specifically comprises:
- applying different-power pump light effects to semiconductors with one doping concentration, to perform imaging measurement respectively; or
- applying same-power pump light effects to semiconductors with different doping concentrations, to perform imaging measurement respectively; or
- applying different external bias electric fields to semiconductors with one doping concentration, to perform imaging measurement respectively; or
- applying the same external bias electric field to semiconductors with different doping concentrations, to perform imaging measurement respectively.

38. The application of a terahertz temporal and spatial resolution imaging system according to claim 35, wherein the step of using the digital holographic reconstruction algorithm for the image reconstruction and optimization on the original experimental data specifically comprises: using an inverse diffraction digital image reconstruction algorithm for the image reconstruction and optimization on the original image data.

39. The application of a terahertz temporal and spatial resolution imaging system according to claim 38, wherein the inverse diffraction digital image reconstruction algorithm is an inverse Fresnel diffraction algorithm.

40. The application of a terahertz temporal and spatial resolution imaging system according to claim 35, wherein the step of analyzing the movement rule of the light-induced carriers of the test sample comprises:
- using a continuity equation to study a rule of diffusion movement of the semiconductor light-induced carriers, specifically, according to distribution of conductivity of semiconductors obtained from a step of applying different-power pump light effects to semiconductors with one doping concentration, to perform imaging measurement respectively and applying same-power pump light effects to semiconductors with different doping concentrations, to perform imaging measurement respectively, analyzing composite effect of light-induced carriers during diffusion, that is, influences of concentration gradient of the light-induced carriers and collision between the light-induced carriers on the diffusion movement of the light-induced carriers, estimating the service life of the semiconductor light-induced carriers, and analyzing proportions of the composite caused by direct collision between the light-induced carriers and the composite caused by lattice defects;
- using a continuity equation to study a rule of drift movement of the semiconductor light-induced carriers, specifically, according to distribution of conductivity of semiconductors obtained from a step of applying different external bias electric fields to the semiconductors with one doping concentration, to perform imaging measurement respectively and applying the same external bias electric field to the semiconductors with different doping concentrations, to perform imaging measurement respectively, analyzing influences of intensity of external electric fields, the light-induced carriers, influences of scattering between impurities and phonons on drift movement of the light-induced carriers; and
- using a continuity equation to uniformly consider the diffusion movement and the drift movement of the semiconductor light-induced carriers, to analyze temporal and spatial distribution characteristics and semiconductor phase transition of the semiconductor light-induced carriers.

* * * * *